(12) United States Patent
Urushitani et al.

(10) Patent No.: US 12,215,142 B2
(45) Date of Patent: Feb. 4, 2025

(54) ANTIBODY FRAGMENT DEGRADING AND REMOVING ABNORMAL TDP-43

(71) Applicant: NATIONAL UNIVERSITY CORPORATION SHIGA UNIVERSITY OF MEDICAL SCIENCE, Otsu (JP)

(72) Inventors: Makoto Urushitani, Otsu (JP); Yoshitaka Tamaki, Otsu (JP)

(73) Assignee: NATIONAL UNIVERSITY CORPORATION SHIGA UNIVERSITY OF MEDICAL SCIENCE, Otsu (JP)

(*) Notice: Subject to any disclaimer, the term of this patent is extended or adjusted under 35 U.S.C. 154(b) by 1136 days.

(21) Appl. No.: 16/980,667

(22) PCT Filed: Mar. 15, 2019

(86) PCT No.: PCT/JP2019/010771
§ 371 (c)(1),
(2) Date: Sep. 14, 2020

(87) PCT Pub. No.: WO2019/177138
PCT Pub. Date: Sep. 19, 2019

(65) Prior Publication Data
US 2021/0024621 A1 Jan. 28, 2021

(30) Foreign Application Priority Data
Mar. 16, 2018 (JP) .................. 2018-049752

(51) Int. Cl.
*C07K 16/18* (2006.01)
*A61P 25/28* (2006.01)
*A61K 39/00* (2006.01)
*A61K 48/00* (2006.01)

(52) U.S. Cl.
CPC .............. *C07K 16/18* (2013.01); *A61P 25/28* (2018.01); *A61K 2039/505* (2013.01); *A61K 48/00* (2013.01); *C07K 2317/24* (2013.01); *C07K 2317/565* (2013.01); *C07K 2317/567* (2013.01); *C07K 2317/622* (2013.01); *C07K 2317/76* (2013.01); *C07K 2317/94* (2013.01)

(58) Field of Classification Search
CPC .......... A61K 2039/505; C07K 2319/01; C07K 2319/02
USPC ............................................ 424/133.1, 135.1
See application file for complete search history.

(56) References Cited

U.S. PATENT DOCUMENTS 9,334,331 B2 * 5/2016 Igawa ........................ A61P 7/04
10,421,807 B2 * 9/2019 Gonzales ................ A61P 17/08

2011/0287453 A1 11/2011 Hasegawa et al.
2018/0305464 A1 10/2018 Li et al.
2020/0010570 A1 1/2020 Li et al.

FOREIGN PATENT DOCUMENTS

| CN | 107151269 A | 9/2017 |
| JP | 2013-162772 A | 8/2013 |
| JP | 2014-171425 A | 9/2014 |
| WO | 2009/008529 A1 | 1/2009 |
| WO | 2013/061163 A2 | 5/2013 |

OTHER PUBLICATIONS

Tamaki (Nature (2018) 8:6030 I; pp. 1-16 ).*
Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Heale et al (Alzheimer's and Dementia, (Jul. 2018) vol. 14, No. 7, Supp. Supplement, pp. P1294-P1295. Meeting Info: Alzheimer's Association International Conference 2018. Chicago, IL, United States. Jul. 22-Jul. 26, 2018 (abstract).*
Office Action dated Oct. 28, 2022 for corresponding Chinese Patent Application No. 201980027565.X, 8 pages.
International Search Report (with English translation) mailed Jun. 4, 2019 for corresponding International Application No. PCT/JP2019/010771, 5 pages.
Tamaki et al., "Degradative intrabody for selective elimination of pathogenic TDP-43 aggregates in vitro and in murine embryos' cerebrum", Journal of Neurological Sciences, 2017, vol. 381, p. 715, Abstract No. 1984.
Tamaki et al., "Elimination of TDP-43 inclusions linked to amyotrophic lateral sclerosis by a misfolding-specific Intrabody with dual proteolytic signals", Scientic Reports, Apr. 16, 2018, vol. 8, Article No. 6030, 16 pages.
Urushitani et al., "Therapeutic effects of immunization with mutant superoxide dismutase in mice models of amyotrophic lateral sclerosis", Proceedings of the National Academy of Sciences, Feb. 13, 2007, vol. 104, No. 7, pp. 2495-2500.
Shodai et al., "Aberrant Assembly of RNA Recognition Motif 1 Links to Pathogenic Conversion of TAR DNA-binding Protein of 43 kDa (TDP-43)", the Journal of Biological Chemistry, May 24, 2013, vol. 288, No. 21, pp. 14886-14905.
Tamaki et al., "The development of therapeutic intrabody against misfolded/mislocalized TDP-43 for ALS", Clinical Neurology, 2016, vol. 56, S370, Pe-045-6, 1 page.
Extended European Search Report dated Nov. 16, 2021 for corresponding European Patent Application No. 19768492.1, 13 pages.
Christian Münz, "Antigen processing via autophagy—not only for MHC class II presentation anymore?", Current Opinion in Immunology, 2010, vol. 22, No. 1, pp. 89-93.

(Continued)

*Primary Examiner* — Lynn A Bristol
(74) *Attorney, Agent, or Firm* — MH2 Technology Law Group, LLP

(57) ABSTRACT

A modified antibody fragment comprising an antibody fragment capable of binding to misfolded TDP-43, and a chaperone-mediated autophagy localizing signal peptide.

6 Claims, 7 Drawing Sheets
Specification includes a Sequence Listing.

(56) References Cited

OTHER PUBLICATIONS

Makoto Urushitani, "The role of TDP-43 in ALS pathogenesis", Neurological Therapeutics, 2017, vol. 34, No. 2, pp. 72-78 with English abstract.
Khalid et al., "Immune Modulation in the Treatment of Amyotrophic Lateral Sclerosis: A Review of Clinical Trials", Frontiers in Neurology, 2017, vol. 8, Article 486, 11 pages.
Uchida et al., "CUL2-mediated clearance of misfolded TDP-43 is paradoxically affected by VHL in oligodendrocytes In ALS", Scientific Reports, 2016, vol. 6, 19118, 19 pages.
Pozzi et al., "Virus-mediated delivery of antibody targeting TAR DNA-binding protein-43 mitigates associated neuropathology", The Journal of Clinical Investigation, 2019, vol. 129, No. 4, pp. 1581-1595.

\* cited by examiner

SEQUENCE LISTING

```
<160> NUMBER OF SEQ ID NOS: 28

<210> SEQ ID NO 1
<211> LENGTH: 8
<212> TYPE: PRT
<213> ORGANISM: Mus musculus

<400> SEQUENCE: 1

Gly Phe Asn Ile Lys Asp Tyr Tyr
1               5

<210> SEQ ID NO 2
<211> LENGTH: 8
<212> TYPE: PRT
<213> ORGANISM: Mus musculus

<400> SEQUENCE: 2

Ile Asp Pro Glu Asp Gly Glu Thr
1               5

<210> SEQ ID NO 3
<211> LENGTH: 13
<212> TYPE: PRT
<213> ORGANISM: Mus musculus

<400> SEQUENCE: 3

Thr Ile Ile Tyr Tyr Tyr Gly Ser Arg Tyr Val Asp Tyr
1               5                   10
```

```
<210> SEQ ID NO 4
<211> LENGTH: 7
<212> TYPE: PRT
<213> ORGANISM: Mus musculus

<400> SEQUENCE: 4

Ser Ser Ile Ser Ser Ser Tyr
1               5

<210> SEQ ID NO 5
<211> LENGTH: 9
<212> TYPE: PRT
<213> ORGANISM: Mus musculus

<400> SEQUENCE: 5

Gln Gln Gly Ser Ser Ile Pro Leu Thr
1               5

<210> SEQ ID NO 6
<211> LENGTH: 414
<212> TYPE: PRT
<213> ORGANISM: Homo sapiens

<400> SEQUENCE: 6

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270
```

```
Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
        290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
            325                 330                 335

Met Gly Met Leu Ala Ser Gln Gln Asn Gln Ser Gly Pro Ser Gly Asn
                340                 345                 350

Asn Gln Asn Gln Gly Asn Met Gln Arg Glu Pro Asn Gln Ala Phe Gly
            355                 360                 365

Ser Gly Asn Asn Ser Tyr Ser Gly Ser Asn Ser Gly Ala Ala Ile Gly
        370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
            405                 410
```

<210> SEQ ID NO 7
<211> LENGTH: 1245
<212> TYPE: DNA
<213> ORGANISM: Homo sapiens

<400> SEQUENCE: 7

```
atgtctgaat atattcgggt aaccgaagat gagaacgatg agcccattga ataccatcg      60
gaagacgatg ggacggtgct gctctccacg gttacagccc agtttccagg ggcgtgtggg    120
cttcgctaca ggaatccagt gtctcagtgt atgagaggtg tccggctggt agaaggaatt    180
ctgcatgccc agatgctggc tggggaaaat ctggtgtatg ttgtcaacta tccaaaagat    240
aacaaaagaa aaatggatga acagatgctc tcatcagcag tgaaagtgaa agagcagtc    300
cagaaaacat ccgatttaat agtgttgggt ctcccatgga aaacaaccga caggacctg    360
aaagagtatt ttagtaccct tggagaagtt cttatggtgc aggtcaagaa agatcttaag    420
actggtcatt caagggggtt tggctttgtt cgttttacgg aatatgaaac acaagtgaaa    480
gtaatgtcac agcgacatat gatagatgga cgatggtgtg actgcaaact tcctaattct    540
aagcaaagcc aagatgagcc tttgagaagc agaaaagtgt ttgtggggcg ctgtacagag    600
gacatgactg aggatgagct gcgggagttc ttctctcagt acggggatgt gatggatgtc    660
ttcatcccca agccattcag ggcctttgcc tttgttacat ttgcagatga tcagattgcg    720
cagtctcttt gtggagagga cttgatcatt aaaggaatca gcgttcatat atccaatgcc    780
gaacctaagc acaatagcaa tagacagtta gaaagaagtg aagatttgg tggtaatcca    840
ggtggctttg ggaatcaggg tggatttggt aatagcagag gggtggagc tggtttggga    900
aacaatcaag gtagtaatat gggtggtggg atgaactttg gtgcgttcag cattaatcca    960
gccatgatgg ctgccgccca ggcagcacta cagagcagtt ggggtatgat gggcatgtta   1020
gccagccagc agaaccagtc aggcccatcg gtaataacc aaaaccaagg caacatgcag   1080
agggagccaa accaggcctt cggttctgga ataactctt atagtggctc taattctggt   1140
gcagcaattg gttggggatc agcatccaat gcagggtcgg gcagtggttt taatggaggc   1200
tttggctcaa gcatggattc taagtcttct ggctggggaa tgtag                   1245
```

```
<210> SEQ ID NO 8
<211> LENGTH: 5
<212> TYPE: PRT
<213> ORGANISM: Artificial Sequence
<220> FEATURE:
<223> OTHER INFORMATION: CMA-targeting motif

<400> SEQUENCE: 8

Lys Phe Arg Glu Gln
1               5

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
gactcgagtc gacatcgatt tttttttttt ttttt                              35

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
ctcaattttc ttgtccacct tggtgc                                        26

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
gactcgagtc gacatcgatt tttttttttt ttttt                              35

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
ctcattcctg ttgaagctct tgacaatggg                                    30

<210> SEQ ID NO 13
<211> LENGTH: 5
<212> TYPE: PRT
<213> ORGANISM: Artificial Sequence
<220> FEATURE:
<223> OTHER INFORMATION: linker

<400> SEQUENCE: 13

Gly Gly Gly Gly Ser
1               5

<210> SEQ ID NO 14
<211> LENGTH: 34
<212> TYPE: DNA
<213> ORGANISM: Artificial Sequence
<220> FEATURE:
```

<223> OTHER INFORMATION: primer

<400> SEQUENCE: 14
tgaaccgcct ccacctattt ccaactttgt cccc                                34

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
ggcggtggcg gatctgaggt tcagctgcag cagt                                34

<210> SEQ ID NO 16
<211> LENGTH: 50
<212> TYPE: DNA
<213> ORGANISM: Artificial Sequence
<220> FEATURE:
<223> OTHER INFORMATION: primer

<400> SEQUENCE: 16
cgagcatgca tctagaaaat tcagagaaca atgatctaga gggccctatt              50

<210> SEQ ID NO 17
<211> LENGTH: 50
<212> TYPE: DNA
<213> ORGANISM: Artificial Sequence
<220> FEATURE:
<223> OTHER INFORMATION: primer

<400> SEQUENCE: 17
aatagggccc tctagatcat tgttctctga attttctaga tgcatgctcg              50

<210> SEQ ID NO 18
<211> LENGTH: 41
<212> TYPE: DNA
<213> ORGANISM: Artificial Sequence
<220> FEATURE:
<223> OTHER INFORMATION: primer

<400> SEQUENCE: 18
gcccaggccc gaattcgcca tggaaattgt gctcacccag t                       41

<210> SEQ ID NO 19
<211> LENGTH: 53
<212> TYPE: DNA
<213> ORGANISM: Artificial Sequence
<220> FEATURE:
<223> OTHER INFORMATION: primer

<400> SEQUENCE: 19
tagatgcatg ctcgagttat tgttctctga atttcaggtc ctcctctgag atc          53

<210> SEQ ID NO 20
<211> LENGTH: 10
<212> TYPE: PRT
<213> ORGANISM: Mus musculus

<400> SEQUENCE: 20

Arg Ile Asp Pro Glu Asp Gly Glu Thr Lys
1               5                   10

<210> SEQ ID NO 21

<211> LENGTH: 119
<212> TYPE: PRT
<213> ORGANISM: Mus musculus

<400> SEQUENCE: 21

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Ile Ile Tyr Tyr Tyr Gly Ser Arg Tyr Val Asp Tyr Trp Gly Gln
            100                 105                 110

Gly Thr Thr Leu Thr Val Ser
        115

<210> SEQ ID NO 22
<211> LENGTH: 107
<212> TYPE: PRT
<213> ORGANISM: Mus musculus

<400> SEQUENCE: 22

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Ser
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Leu Thr Phe Gly Ser Gly Thr Lys Leu Glu Ile
            100                 105

<210> SEQ ID NO 23
<211> LENGTH: 357
<212> TYPE: DNA
<213> ORGANISM: Mus musculus

<400> SEQUENCE: 23
gaggttcagc tgcagcagtc tggggcagag cttgtgaagc caggggcctc agtcaagttg      60
tcctgcacag cttctggctt caacattaaa gactactata tgcactgggt gaagcagagg     120
actgaacagg gcctggagtg gattggaagg attgatcctg aggatggtga aactaaatat     180
gccccgaaat tccagggcaa ggccactatt acagcagaca catcctccaa cacagcctac     240
ctgcagctca gcagcctgac atctgaggac actgccgtct attactgtac tatcatttat     300
tactacggta gtcgctacgt tgactactgg ggccaaggca ccactctcac agtctcc       357

```
<210> SEQ ID NO 24
<211> LENGTH: 321
<212> TYPE: DNA
<213> ORGANISM: Mus musculus

<400> SEQUENCE: 24
gaaattgtgc tcacccagtc tccaaccacc atggctgcat ctcccgggga gaagatcact      60
atcacctgca gtgccagctc aagtataagt tccagttact tgcattggta tcagcagaag     120
ccaggattct cccctaaact cttgatttat aggacatcca atctggcttc tggagtccca     180
gctcgcttca gtggcagtgg gtctgggacc tcttactctc tcacaattgg caccatggag     240
gctgaagatg ttgccactta ctactgccag cagggtagta gtataccact cacgttcggc     300
tcggggacaa agttggaaat a                                               321

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
caagatcacc atcaccaacg                                                  20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
tcgtcctccg ctttgtactt                                                  20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gcaccgtcaa ggctgagaac                                                  20

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
tggtggtgaa gacgccagtg ga                                               22
```

ANTIBODY FRAGMENT DEGRADING AND REMOVING ABNORMAL TDP-43

CROSS-REFERENCE TO RELATED APPLICATIONS

This application is a U.S. National Stage application of PCT/JP2019/010771 filed 15 Mar. 2019, which claims priority to Japanese Application No. 2018-049752 filed 16 Mar. 2018, the entire disclosures of which are hereby incorporated by reference in their entireties.

SEQUENCE LISTING

The present application contains a Sequence Listing which has been submitted electronically in ASCII format and is hereby incorporated by reference in its entirety. Said ASCII copy, created on 10 Sep. 2020, is named P19-052WO_SEQUENCE_LISTING.txt and is 13 kilobytes in size.

TECHNICAL FIELD

The present invention relates to a modified antibody fragment degrading and removing TDP-43 having a structural abnormality. Further, the present invention relates to a nucleic acid encoding the modified antibody fragment, an expression vector comprising the nucleic acid, and a gene therapeutic agent comprising the nucleic acid.

BACKGROUND ART

The nuclear protein TDP-43 (TAR DNA-binding protein of 43 kDa) has been identified as a causative protein of amyotrophic lateral sclerosis (ALS), which is the most refractory neurological disease, and frontotemporal dementia (FTD), which is the second most prevalent form of dementia. TDP-43 escapes from the nucleus in FTD and ALS, and forms pathological aggregates in the cytoplasm; however, its mechanism is unknown.

TDP-43 has been found to be very high in ubiquitinated inclusions in FTD and ALS. At present, diseases with abnormal TDP-43 pathology are classified as a group of diseases called TDP-43 proteinopathy. Various reports have raised the possibility that TDP-43 dysfunction is the essence of ALS pathology.

Thus, elucidating the physiological and pathological functions of TDP-43 may lead to the conquest of ALS, and vigorous research in this regard is underway around the world. The most obvious and important pathological findings of TDP-43 proteinopathy are decreased nuclear staining of TDP-43 and the formation of inclusions in the cytoplasm. Elucidation of the function of this ectopic localization is essential for understanding the pathophysiology of ALS.

The molecular structure of TDP-43 has two RNA-binding regions (RRM), a C-terminal glycine-rich region, a nuclear localization signal (NLS), and a nuclear export signal (NES). TDP-43 is constitutively expressed in all somatic cells and is mainly localized in the nucleus. In FTD and ALS, TDP-43 is also localized in the nucleus without exception in normal tissues; thus, the influence of ectopic localization of TDP-43 on pathological conditions has been noted. TDP-43-positive cell inclusions frequently contain fragmented and phosphorylated TDP-43.

In addition to FTD and ALS, other reported diseases with ectopic localization of TDP-43 include Perry syndrome, low-grade glioma, Alzheimer's disease, Huntington's disease, Pick's disease, Parkinson's disease, Lewy body disease, corticobasal degeneration, inclusion body myositis, B-cell lymphoma (M stage), and the like.

The present inventors have advanced research from the viewpoints of (1) how TDP-43 transforms from a normal structure, which is unrelated to diseases, to a toxic pathogenic structure, and (2) how to capture the abnormal structure. As a result, it has been proved that the cysteine residues of RRMI in TDP-43 are important for maintaining the normal structure, and that the abnormal modification can reproduce, in vitro, abnormal aggregates observed in the brains of ALS and FTD (PTL 1). Further, it has been reported that an externally exposed sequence in the TDP-43 molecule aberrantly aggregated and abnormally localized in the cytoplasm is identified, and the sequence is targeted, thereby making it possible to predict the risk of developing a disease in which aggregates of TDP-43 accumulate (PTL 2).

In addition, PTL 3 and PTL 4 report antibodies that detect TDP-43. However, aggregates recognized by these antibodies are in an advanced stage, and earlier structural changes are further required as therapeutic targets.

CITATION LIST

Patent Literature

PTL 1: JP2014-171425A
PTL 2: JP2013-162772A
PTL 3: WO2009/008529
PTL 4: WO2013/061163

SUMMARY OF INVENTION

Technical Problem

An object of the present invention is to provide a modified antibody fragment capable of degrading and removing misfolded TDP-43. Another object of the present invention is to provide a nucleic acid encoding the modified antibody fragment, an expression vector comprising the nucleic acid, and a gene therapeutic agent comprising the nucleic acid.

Solution to Problem

As a result of extensive studies to achieve the above objects, the present inventors found that when a chaperone-mediated autophagy (CMA) localizing signal was added to scFv capable of binding to misfolded TDP-43, and the obtained scFv was used as an intracellular antibody, cell death could be suppressed in vitro, and misfolded TDP-43 could be degraded and removed in vivo.

The present invention has been completed upon further studies based on these findings, and provides the following modified antibody fragment, nucleic acid, expression vector, and gene therapeutic agent.

Item 1.

A modified antibody fragment comprising an antibody fragment capable of binding to misfolded TDP-43, and a chaperone-mediated autophagy localizing signal peptide;
the antibody fragment comprising:
a heavy-chain variable region comprising a heavy-chain CDR 1 consisting of an amino acid sequence GFNIKDYY (SEQ ID NO: 1), a heavy-chain CDR 2 consisting of an amino acid sequence IDPEDGET (SEQ ID NO: 2), and a heavy-chain CDR 3 consisting of an amino acid sequence TIIYYYGSRYVDY (SEQ ID NO: 3), the heavy-chain variable region optionally having 3 or fewer amino acid substitutions, and/or a light-chain variable region comprising a light-chain CDR 1 consisting of an amino acid sequence SSISSSY (SEQ ID NO: 4), a light-chain CDR 2 consisting of an amino acid sequence RTS, and a light-chain CDR 3 consisting of an amino acid sequence QQGSSIPLT (SEQ ID NO: 5), the light-chain variable region optionally having 3 or fewer amino acid substitutions; and the antibody fragment being scFv, VH, or VL.

Item 2.

The modified antibody fragment according to Item 1, wherein the antibody fragment is scFv.

Item 3.

The modified antibody fragment according to Item 1 or 2, wherein the antibody fragment is a humanized antibody fragment.

Item 4.

A nucleic acid encoding the modified antibody fragment according to any one of Items 1 to 3.

Item 5.

An expression vector comprising the nucleic acid according to Item 4.

Item 6.

A gene therapeutic agent comprising the nucleic acid according to Item 4.

Item 7.

The therapeutic agent according to Item 6, for use in the treatment of a disease in which aggregates of TDP-43 accumulate.

Item 8.

The therapeutic agent according to Item 7, wherein the disease in which aggregates of TDP-43 accumulate is amyotrophic lateral sclerosis, frontotemporal dementia, or Perry syndrome.

Item 9.

The therapeutic agent according to Item 6, for use in inducing a heat-shock protein.

Item 10.

The therapeutic agent according to Item 9, wherein the heat-shock protein is Hsp70.

Advantageous Effects of Invention

The use of the modified antibody fragment of the present invention as an intracellular antibody makes it possible to degrade and remove misfolded TDP-43, and to suppress neuronal cell death. Therefore, the modified antibody fragment of the present invention can be expected to have a therapeutic effect on diseases in which aggregates of TDP-43 accumulate.

In addition, the modified antibody fragment of the present invention can induce a heat-shock protein. As a result, an effect of loosening aggregates of TDP-43 can be obtained, and degradation by autophagy can be further promoted.

Figure 4:
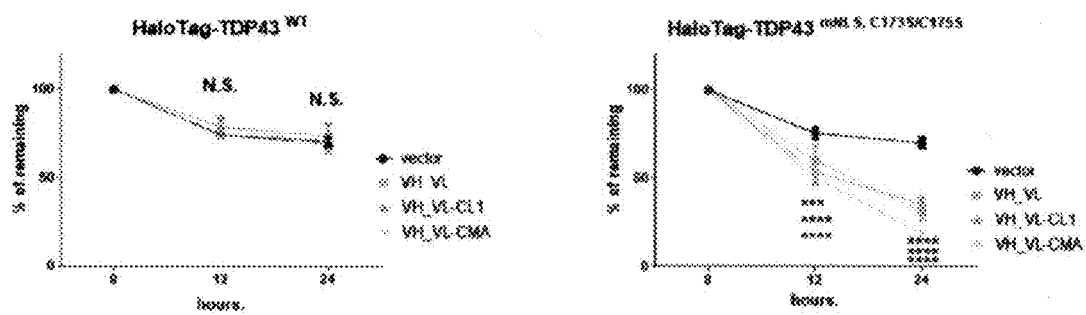
Figure 4:
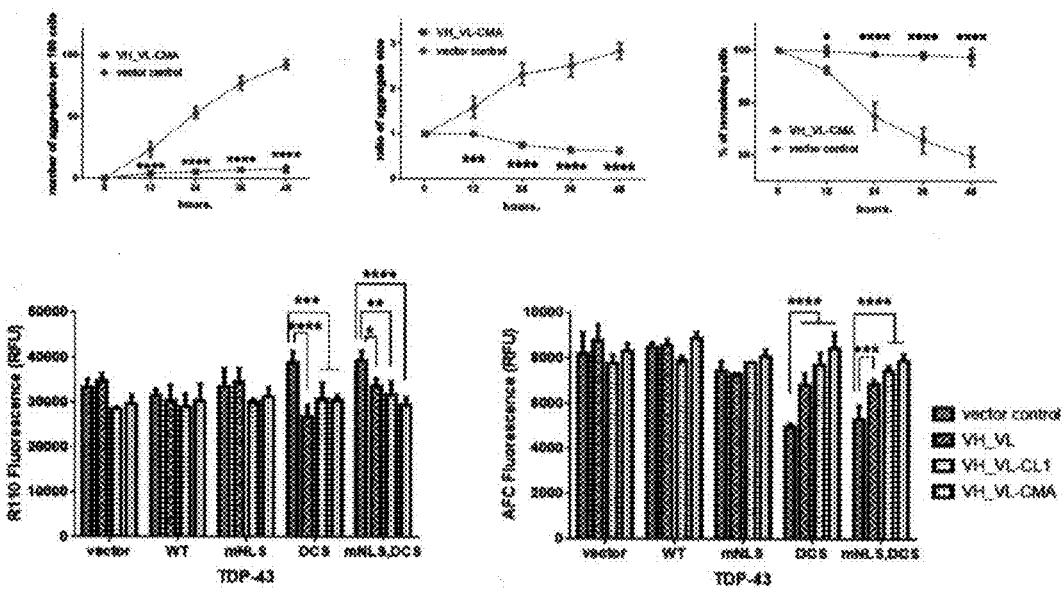

The upper graphs of FIG. 4 show the protective effect of scFv on misfolded TDP-43-induced cell death and aggregate formation. data: mean±SD from three different blindly selected fields of view, $*p<0.05$, $*p<0.005$, $**p<0.001$, compared to the vector control group. The test is based on Dunnett's two-way analysis of variance. The lower graphs of FIG. 4 show that scFv suppresses cell death caused by misfolded TDP-43 and raises the survival rate. n=3, data: mean±SD, $*p<0.05$, $p<0.01$, $*p<0.005$, $****p<0.001$, compared to the vector control group. The test is based on Dunnett's two-way analysis of variance.

Figure 5:
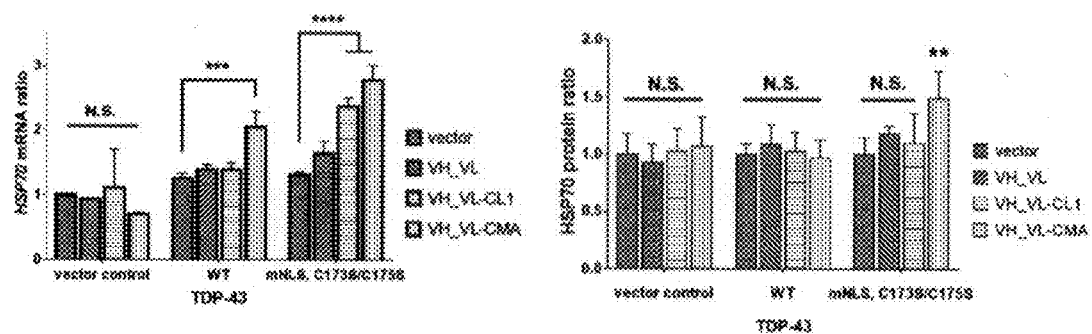

FIG. 5 shows that scFv-CMA induces heat-shock chaperone Hsp70 in the presence of misfolded TDP-43. left: Hsp70 mRNA amount, n=3, data: mean #SD, $*p<0.005$, $p<0.001$, compared to the vector control group. The test is based on Dunnett's two-way analysis of variance. N.S. indicates not significant. right: Hsp70 protein amount, data: mean #SD, from three independent experiments. Each data was normalized with actin. $p<0.01$, compared to the vector control group. The test is based on Dunnett's two-way analysis of variance. N.S. indicates not significant.

Figure 6:
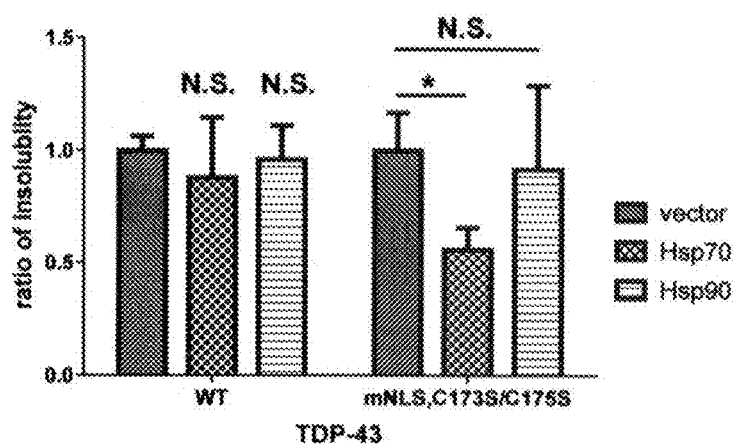

FIG. 6 shows that Hsp70 solubilizes aggregates of misfolded TDP-43. mean±SD, from three independent experiments. Each data was normalized with actin. $*p<0.05$, compared to the vector control group. The test is based on Dunnett's two-way analysis of variance. N.S. indicates not significant.

Figure 7:
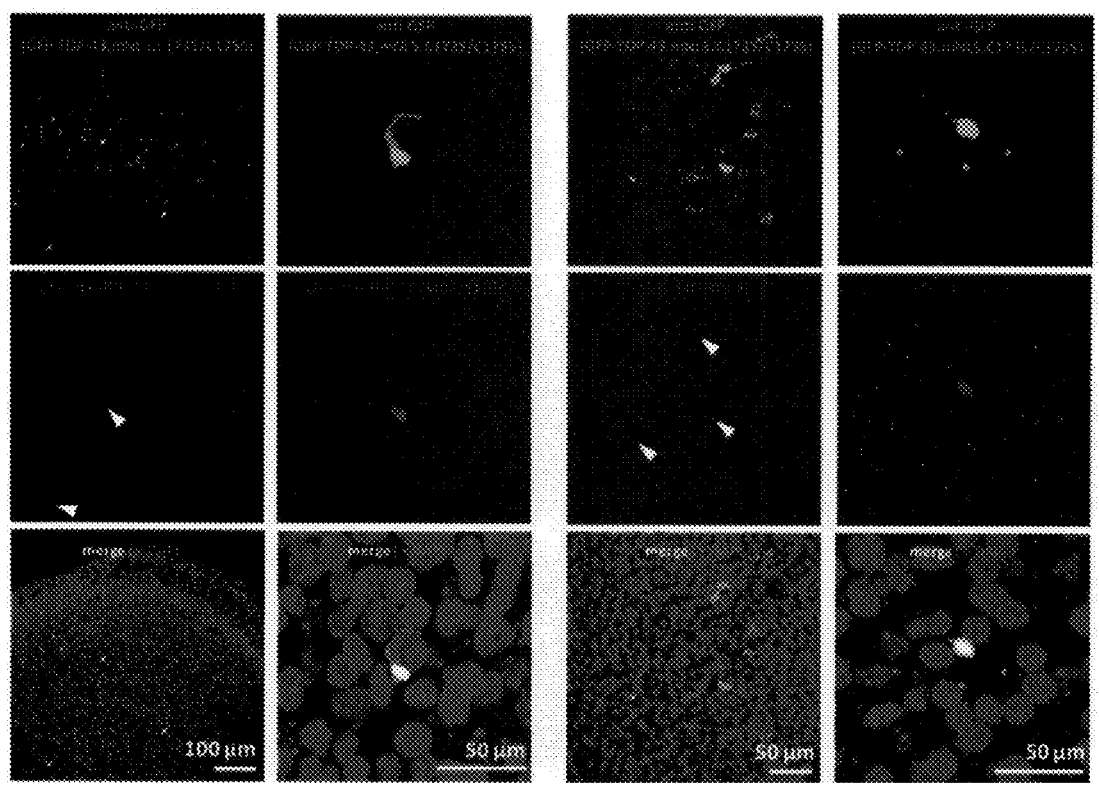

FIG. 7 shows that exogenous misfolded TDP-43 introduced into the brain by in utero electroporation forms ubiquitin- and phosphorylated TDP-43-positive aggregates, as in ALS patients.

Figure 8:
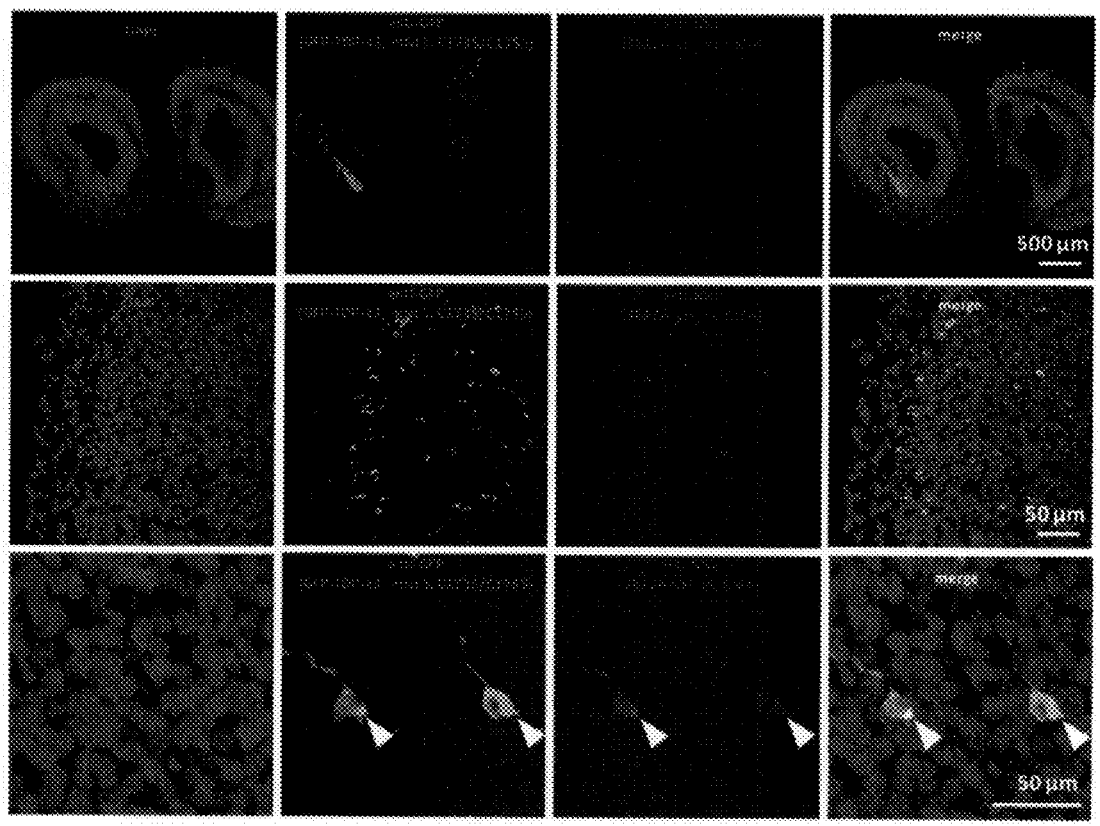

FIG. 8 shows that exogenous misfolded TDP-43 and scFv-CMA introduced into the brain by in utero electroporation coexist in the brain aggregates.

Figure 9:
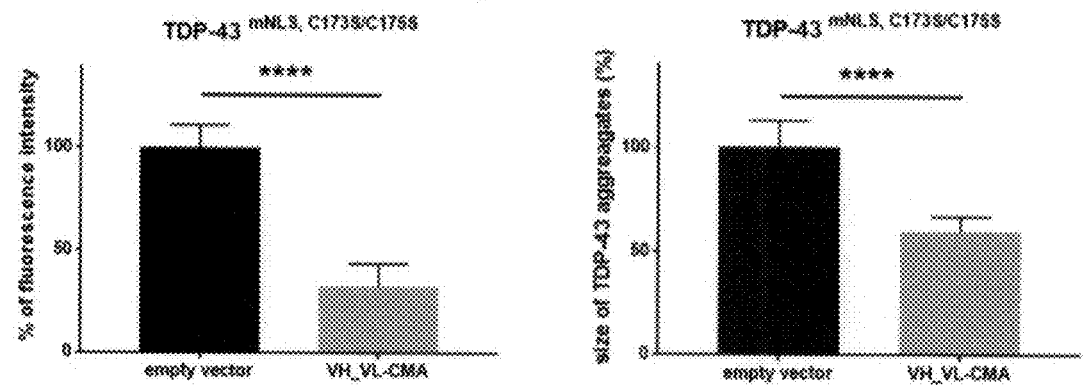

FIG. 9 shows that TDP-43 aggregates in the fetal brain introduced by in utero electroporation decrease by co-expression of scFv-CMA. data: mean±SD, n=7, $****p<0.001$, compared to the vector control group. The test is based on the unpaired t-test.

Figure 10:
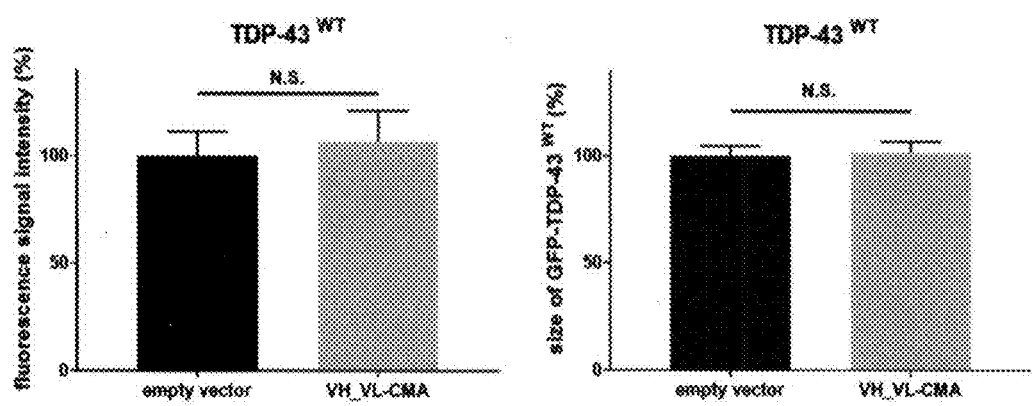

FIG. 10 shows that wild-type TDP-43 in the fetal brain introduced by intrauterine electroporation does not decrease by co-expression of scFv-CMA. data: mean±SD, n=7. The test is based on the unpaired t-test. N.S. indicates not significant.

Figure 11:
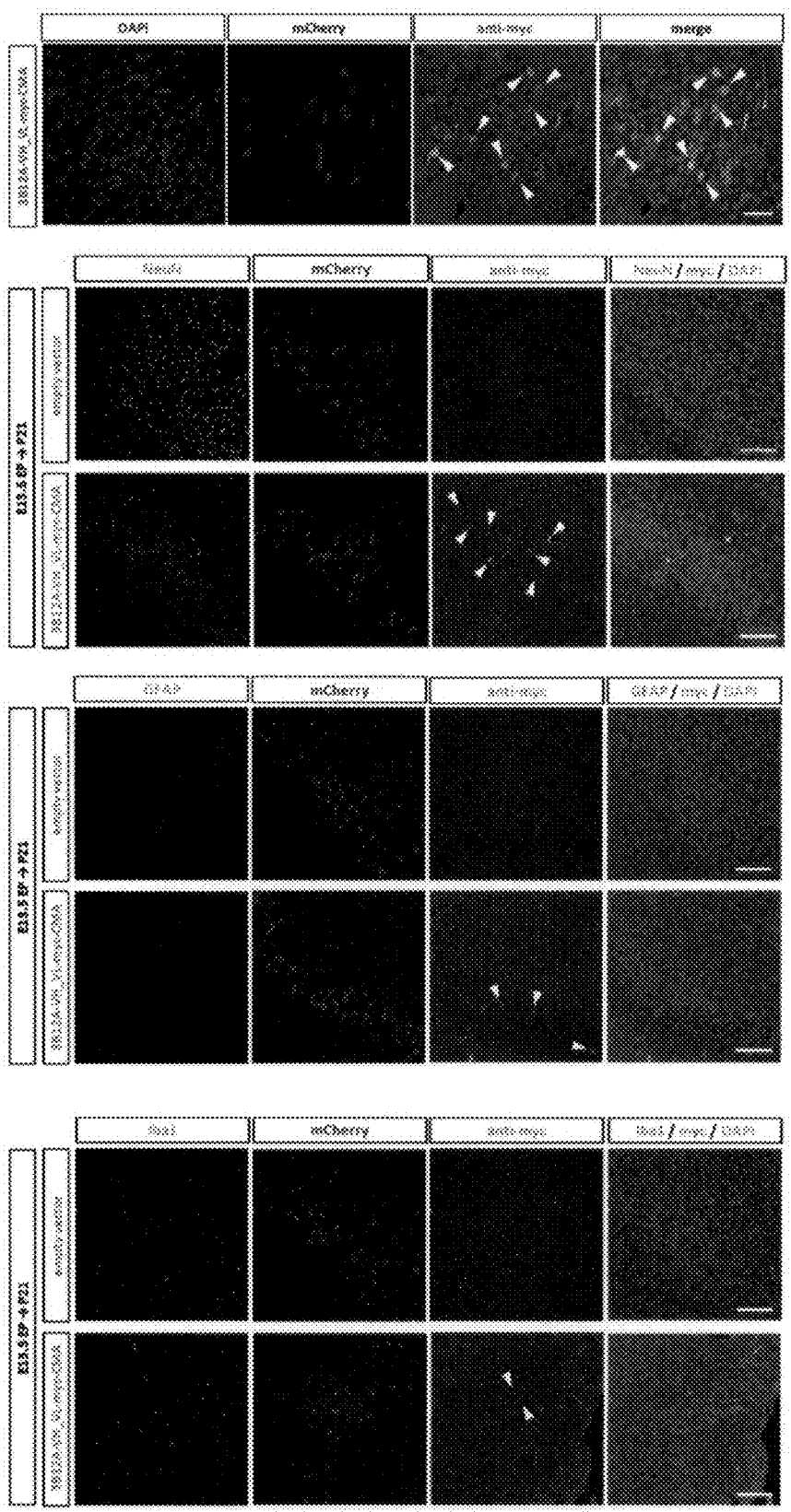

FIG. 11 shows that scFv-Myc-CMA expressed by in utero electroporation in the fetal period does not affect the early development of mice, and does not induce neurotoxicity or abnormal gliosis in the brain. scale bar=100 μm

DESCRIPTION OF EMBODIMENTS

The present invention will be described in detail below.

In the present specification, the term "comprise" includes the meanings of "essentially consist of" and "consist of."

In the present invention, the term "gene" includes double-stranded DNA, single-stranded DNA (sense strand or antisense strand), and fragments thereof, unless otherwise specified. Further, in the present invention, the term "gene" refers to a regulatory region, a coding region, an exon, and an intron without distinction, unless otherwise specified.

In the present invention, the terms "nucleic acid," "nucleotide," and "polynucleotide" have the same meaning and include both DNA and RNA, which may be double-stranded or single-stranded.

The Ref Seq IDs shown below are registered on the NCBI website.

The modified antibody fragment of the present invention is characterized by comprising an antibody fragment capable of binding to misfolded TDP-43, and a chaperone-mediated autophagy localizing signal peptide;

the antibody fragment comprising:
a heavy-chain variable region comprising a heavy-chain CDR 1 consisting of an amino acid sequence GFNIKDYY (SEQ ID NO: 1), a heavy-chain CDR 2 consisting of an amino acid sequence IDPEDGET (SEQ ID NO: 2), and a heavy-chain CDR 3 consisting of an amino acid sequence TIIYYYGSRYVDY (SEQ ID NO: 3), the heavy-chain variable region optionally having 3 or fewer amino acid substitutions, and/or
a light-chain variable region comprising a light-chain CDR 1 consisting of an amino acid sequence SSISSSY (SEQ ID NO: 4), a light-chain CDR 2 com consisting of an amino acid sequence RTS, and a light-chain CDR 3 consisting of an amino acid sequence QOGSSIPLT (SEQ ID NO: 5), the light-chain variable region optionally having 3 or fewer amino acid substitutions; and
the antibody fragment being scFv, VH, or VL.

TDP-43 in the present invention is generally derived from an animal, preferably derived from a mammal, and particularly preferably derived from a human.

Human-derived TDP-43 is a protein comprising 414 amino acids, and its primary structure has high homology to the heterogeneous nuclear ribonucleoprotein (hnRNA) family. TDP-43 has two highly conserved RNA recognition motifs (RRM1 and RRM2), and contains a glycine-rich region on the C-terminal side, which binds to the members of the hnRNP family.

The amino acid sequence of human-derived TDP-43 protein is registered as Ref Seq Accession No. NP_031401, and is shown in SEQ ID NO: 6. Moreover, the gene encoding human-derived TDP-43 protein is registered as Ref Seq Accession No. NM_007375, and the base sequence thereof is shown in SEQ ID NO: 7.

TDP-43 in the present invention may be a variant of a protein comprising the amino acid sequence represented by SEQ ID NO: 6, as long as it has a biological activity equivalent to that of the protein comprising the amino acid sequence represented by SEQ ID NO: 6.

Misfolded TDP-43 refers to TDP-43 folded into a structure different from the natural structure, and particularly to TDP-43 having a pathogenic structure associated with TDP-43 proteinopathy.

The complementarity-determining region (CDR) contained in the antibody fragment of the present invention is characterized by being capable of binding to misfolded TDP-43. It is desirable that the antibody fragment of the present invention specifically binds to misfolded TDP-43 and does not bind to TDP-43 having the normal structure.

The antibody fragment of the present invention preferably comprises:
a heavy-chain variable region comprising a heavy-chain CDR1 consisting of an amino acid sequence GFNIKDYY (SEQ ID NO: 1), a heavy-chain CDR2 consisting of an amino acid sequence IDPEDGET (SEQ ID NO: 2), and a heavy-chain CDR3 consisting of an amino acid sequence TIIYYYGSRYVDY (SEQ ID NO: 3), the heavy-chain variable region optionally having 3 or fewer amino acid substitutions; and
a light-chain variable region comprising a light-chain CDR1 consisting of an amino acid sequence SSISSSY (SEQ ID NO: 4), a light-chain CDR2 consisting of an amino acid sequence RTS, and a light-chain CDR3 consisting of an amino acid sequence QOGSSIPLT (SEQ ID NO: 5), the light-chain variable region optionally having 3 or fewer amino acid substitutions.

Since the heavy-chain CDR 2 used in the present invention contains a PEST sequence, it has the property of being rapidly degraded in the absence of misfolded TDP-43.

Amino acid substitution is performed so that the binding of the antibody fragment to misfolded TDP-43 is maintained. The phrase "optionally having 3 or fewer amino acid substitutions" means that a total of 3 or fewer amino acids may be substituted in the heavy-chain variable region or light-chain variable region. Amino acid substitution is preferably performed in the CDR.

The number of amino acid substitutions is preferably 2 or fewer, more preferably 1 or fewer, and even more preferably 0. When amino acid substitution is performed, it is considered that the activity of the original antibody fragment is likely to be maintained by substitution with an amino acid having similar properties. Techniques for amino acid substitution in a specific amino acid sequence are known.

scFv refers to an antibody fragment in which Fv comprising a heavy-chain variable region and a light-chain variable region is connected by an appropriate peptide linker. VH and VL refer, respectively, to an antibody fragment consisting of a heavy-chain variable region, and an antibody fragment consisting of a light-chain variable region.

The antibody fragment of the present invention is preferably scFv. scFv can be one in which VH and VL are connected in any order.

The sequence of the framework region (FR region) in the variable region of the antibody fragment of the present invention is not particularly limited, as long as the antibody fragment is capable of binding to misfolded TDP-43, and any sequence can be used. The antibody fragment of the present invention is preferably a humanized antibody fragment having a human-derived framework region. Such a humanized antibody can be prepared by a known method.

The chaperone-mediated autophagy (CMA) localizing signal peptide refers to a signal peptide that induces localization to CMA. CMA refers to a pathway in which a protein is recognized by a chaperone, and the complex is translocated into a lysosome through binding with LAMP2A, which is considered to be a receptor on the lysosome, and is degraded. Thus, the presence of CMA in the modified antibody fragment of the present invention promotes autophagy degradation of misfolded TDP-43 binding to the antibody fragment.

Any chaperone-mediated autophagy (CMA) localizing signal peptide can be used without particular limitation, as long as it is a signal peptide that can induce localization to CMA. Examples thereof include a peptide comprising an amino acid sequence KFREQ (SEQ ID NO: 8).

In the modified antibody fragment of the present invention, the antibody fragment and the chaperone-mediated autophagy localizing signal peptide may be bonded in any order, as long as the effects of the present invention can be obtained. In addition, these may be directly bonded, or any amino acid sequence may exist between them. In addition to the antibody fragment and peptide, other proteins and peptides may be bound to the modified antibody fragment of the present invention.

The nucleic acid of the present invention is characterized by encoding the modified antibody fragment described above. The nucleic acid can be prepared by a conventional method, such as biochemical cleavage/recombination, using nucleic acids encoding each of the antibody fragment and the peptide, which constitute the modified antibody fragment. The nucleic acids encoding the antibody fragment and the chaperone-mediated autophagy localization signal peptide can be prepared by conventional methods, such as PCR, chemical synthesis, and biochemical cleavage/recombination.

The expression vector of the present invention is characterized by comprising the nucleic acid described above. The expression vector is not particularly limited, and known expression vectors can be widely used. A suitable expression vector may be appropriately selected in consideration of, for example, the type of cells into which the nucleic acid is transferred. The expression vector may contain a promoter, an enhancer, a terminator, a polyadenylation signal, a selection marker, an origin of replication, and the like, in addition to the above nucleic acid. The expression vector may be either an autonomously replicating vector, or a vector that is integrated into the genome of a host cell when transferred into the host cell, and that is replicated together with the integrated chromosome. The above nucleic acid can be inserted into the expression vector by a known method.

It is well known how to construct the expression vector and how to transfer the expression vector into cells. For example, reference may be made to Sambrook and Russell, Molecular Cloning, A Laboratory Manual, 3rd edition, Cold Spring Harbor Laboratory Press (2001).

The gene therapeutic agent of the present invention is characterized by comprising the nucleic acid described above. The modified antibody fragment of the present invention can be used as an intracellular antibody (intrabody) by expressing the nucleic acid in cells using the gene therapeutic agent of the present invention.

In order to express the nucleic acid in cells, for example, a non-viral vector or a viral vector can be used. Examples of non-viral vectors include liposomes, polymer micelles, cationic carriers, and the like. Examples of viral vectors include retrovirus, adenovirus, adeno-associated virus, Sendai virus, bornavirus, and the like. A vector containing the above nucleic acid is introduced into a detoxified virus, and cells or tissues are infected with this virus, whereby the nucleic acid can be introduced into the cells or tissues.

The gene therapeutic agent of the present invention may optionally contain a biologically acceptable carrier, an excipient, and the like, depending on the use form. The gene therapeutic agent of the present invention can be produced by a conventional method. For example, the gene therapeutic agent of the present invention can be used orally as tablets, capsules, elixirs, microcapsules, or the like, optionally with a sugar coating or an enteric coating; transdermally, nasally, or transtracheally as external preparations (e.g., ointments and plasters), sprays, inhalants, or the like; and parenterally in the form of injections, such as sterile solutions or suspensions, with water or other pharmaceutically acceptable liquids.

The amount of the nucleic acid, which is an active ingredient in the gene therapeutic agent of the present invention, is appropriately selected depending on the dosage form, administration route, etc., and is generally about 0.0001 to 90 masst, and preferably about 0.001 to 70 mass %, in the total amount of the preparation.

The gene therapeutic agent of the present invention is administered to mammals including humans. The method for administering the gene therapeutic agent of the present invention is not particularly limited, and can be performed by a method known to those skilled in the art, such as intraarterial injection, intravenous injection, or subcutaneous injection. The dose of the gene therapeutic agent of the present invention can be appropriately determined finally by a doctor's judgement, in consideration of the type of dosage form, the administration method, the age and weight of the patient, the symptoms of the patient, and the like.

The gene therapeutic agent of the present invention can express the modified antibody fragment in cells and degrade and remove misfolded TDP-43, and therefore can be used for the treatment of diseases in which aggregates of TDP-43 accumulate. The diseases in which aggregates of TDP-43 accumulate are not limited to these. Examples thereof include amyotrophic lateral sclerosis, frontotemporal dementia, Perry syndrome, low-grade glioma, Alzheimer's disease, Huntington's disease, Pick's disease, Parkinson's disease, Lewy body disease, corticobasal degeneration, inclusion body myositis, B-cell lymphoma (M stage), and the like. Among these, the gene therapeutic agent of the present invention can be preferably used for amyotrophic lateral sclerosis, frontotemporal dementia, and Perry syndrome.

The gene therapeutic agent of the present invention can also be used to induce a heat-shock protein. The heat-shock protein has the action of loosening aggregates of TDP-43 and promoting its degradation. The heat-shock protein is preferably one that is induced in the presence of a misfolded protein, and examples thereof include Hsp70, Hsp25, Hsp104, Hsp110, and the like. Among these, Hsp70 is preferable.

When the modified antibody fragment of the present invention is used as an intracellular antibody, it does not affect wild-type TDP-43, can degrade and remove misfolded TDP-43, and can suppress neuronal cell death. Thus, the modified antibody fragment of the present invention has a therapeutic effect on diseases in which aggregates of TDP-43 accumulate.

The modified antibody fragment of the present invention can also induce a heat-shock protein. As a result, an effect of loosening aggregates of TDP-43 can be obtained, and degradation by autophagy can thus be further promoted.

EXAMPLES

Examples will be provided below to describe the present invention in more detail. However, the present invention is not limited to these Examples.

Experimental Method

The materials, reagents, and experimental methods in the following test examples are as follows, unless otherwise stated.

Production of scFv

From mouse hybridomas, a commercial mRNA extraction kit (Invitrogen, Carlsbad, CA, USA) and cDNA synthesis kit (SUPERSCRIPT™ III Reverse Transcriptase (Invitrogen)) were used to prepare, respectively, messenger RNA and cDNA with an oligo dT primer using the messenger RNA as a template. A primer pair of 5'-GAC TCG AGT CGA CAT CGA TTT TTT TTT TTT TT-3' (SEQ ID NO: 9) and 5'-CTC AAT TTT CTT GTC CAC CTT GGT GC-3' (SEQ ID NO: 10) was used to clone VH cDNA, and a primer pair of 5'-GAC TCG AGT CGA CAT CGA TTT TTT TTT TTT TTT TT-3' (SEQ ID NO: 11) and 5'-CTC ATT CCT GTT GAA GCT CTT GAC AAT GGG-3' (SEQ ID NO: 12) was used to clone VL cDNA, by conventional PCR amplification.

VH and VL were linked by a linker sequence in which three GGGGS (SEQ ID NO: 13) were connected in tandem (5'-tgaaccgcctccaccTATTTCCAACTTTGTCCCC-3' (SEQ ID NO: 14), 5'-ggcggtggcggatct-GAGGTTCAGCTGCAGCAGT-3' (SEQ ID NO: 15)). Further, chaperone-mediated autophagy signal (CMA) amino acid sequences KFREQ (5'-CGAGCATG-CATCTAGAAAATTCAGAGAACAATGATCTAGAGG-GCCCTATT-3' (SEQ ID NO: 16), 5'-AATAGGGCCCTCTAGATCATTGTTCTCTGAAT-TTTCTAGATGCATGCTCG-3' (SEQ ID NO: 17)) and Myc tags (5'-GCCCAGGCCCGAATTCGCCATGgAAAT-TGTGCTCACCCAGT-3' (SEQ ID NO: 18), 5'-TAGATG-CATGCTCGAGTTATTGTTCTCTGAAT-TTCAGGTCCTCCTCTGAGATC-3' (SEQ ID NO: 19)) were added to the carboxyl terminal. These VH-VL and VL-VH were subcloned into pcDNA3 vector (Invitrogen).

The amino acid sequences of VH and VL encoded by the cloned DNA are shown below. The underlined parts are sequentially CDR1, CDR2, and CDR3. Further, VH contains a PEST sequence (RIDPEDGETK (SEQ ID NO: 20)) in the CDR2. Moreover, the base sequences corresponding to the following amino acid sequences of VH and VL are also shown below.

```
VH (amino acid sequence)
                                            (SEQ ID NO: 21)
EVQLQQSGAELVKPGASVKLSCTASGFNIKDYYMHWVKQRTEQGLEWIGR

IDPEDGETKYAPKFQGKATITADTSSNTAYLQLSSLTSEDTAVYYCTIIY

YYGSRYVDYWGQGTTLTVS

VL (amino acid sequence)
                                            (SEQ ID NO: 22)
EIVLTQSPTTMAASPGEKITITCSASSSISSSYLHWYQQKPGFSPKLLIY

RTSNLASGVPARFSGSGSGTSYSLTIGTMEAEDVATYYCQQGSSIPLTFG

SGTKLEI

VH (base sequence)
                                            (SEQ ID NO: 23)
GAGGTTCAGCTGCAGCAGTCTGGGGCAGAGCTTGTGAAGCCAGGGGCCTC

AGTCAAGTTGTCCTGCACAGCTTCTGGCTTCAACATTAAAGACTACTATA

TGCACTGGGTGAAGCAGAGGACTGAACAGGGCCTGGAGTGGATTGGAAGG

ATTGATCCTGAGGATGGTGAAACTAAATATGCCCCGAAATTCCAGGGCAA

GGCCACTATTACAGCAGACACATCCTCCAACACAGCCTACCTGCAGCTCA

GCAGCCTGACATCTGAGGACACTGCCGTCTATTACTGTACTATCATTTAT

TACTACGGTAGTCGCTACGTTGACTACTGGGGCCAAGGCACCACTCTCAC

AGTCTCC

VL (base sequence)
                                            (SEQ ID NO: 24)
GAAATTGTGCTCACCCAGTCTCCAACCACCATGGCTGCATCTCCCGGGGA

GAAGATCACTATCACCTGCAGTGCCAGCTCAAGTATAAGTTCCAGTTACT

TGCATTGGTATCAGCAGAAGCCAGGATTCTCCCCTAAACTCTTGATTTAT
```

AGGACATCCAATCTGGCTTCTGGAGTCCCAGCTCGCTTCAGTGGCAGTGG

GTCTGGGACCTCTTACTCTCTCACAATTGGCACCATGGAGGCTGAAGATG

TTGCCACTTACTACTGCCAGCAGGGTAGTAGTATACCACTCACGTTCGGC

TCGGGGACAAAGTTGGAAATA

Cultured Cells and Transfection

HEK293A cells and Neuro2a cells were cultured in an incubator at 37° C. with 5% CO$_2$ using Dulbecco's modified Eagle medium (DMEM; Nacalai Tesque, Inc.) supplemented with 10% fetal bovine serum (FBS) and penicillin-streptomycin (100-fold). Plasmid transfection was performed using FuGENE™ HD (Roche) according to the attached document.

Western Blotting Method and Immunoprecipitation Method

HEK293A cells were lysed in RIPA buffer (20 mM HEPES-KOH (pH 7.4), 125 mM NaCl, 2 mM EDTA, 1% NONIDET™-P40, 1% sodium-deoxycholate) containing a protease inhibitor (Roche) to produce a lysate.

Affinity beads (Sigma) with immobilized anti-FLAG antibody were added to the lysate and reacted with stirring at 4° C. for 16 hours. The beads were then washed four times with RIPA buffer, and the proteins bound to the beads were dissolved by reaction with 2% SDS sample buffer at 95° C. for 5 minutes to prepare an immunoprecipitation solution. The total lysate and the immunoprecipitation solution were adjusted to be 2% SDS and 100 mM dithiothreitol (DTT). For Western blotting, a sample was added to a commercial polyacrylamide gel (Wako), electrophoresed, and transferred to a PVDF membrane, followed by reaction with a primary antibody and then with a peroxidase-labeled secondary antibody (Jackson Immunolaboratory), after which color was developed using a commercial chemiluminescence kit (ECL; Thermo-Fisher Scientific or Nacalai Tesque, Inc.).

Immunohistochemical Analysis of Cultured Cells Using Fluorescence Microscope 48 hours after transfection, the cells were fixed by reaction with 4% paraformaldehyde (PFA) at 22° C. for 20 minutes. Thereafter, blocking with 0.1% Triton X100+5% normal goat serum and membrane permeabilization were performed at 22° C. for 1 hour. Reaction with a primary antibody was performed at 4° C. for 16 hours, and further reaction with a fluorescently labeled secondary antibody was performed at 22° C. for 30 minutes. Further, 4'-6 diamidino-2-phenylindole (DAPI) was added as a counterstain. Observation and photography were performed using a confocal laser microscope (FV1000-D IX81, Olympus Corporation).

Sandwich ELISA Method

Sandwich ELISA was performed to quantify the intracellular binding of scFv to an antigen. FLAG-tagged TDP-43 (TDP-43-FLAG) and Myc-tagged scFv (scFv-Myc) were transfected into HEK293A cells using the method described above. 48 hours later, the cells were lysed in RIPA buffer to prepare a lysate. Separately, the lysate was added to an ELISA plate (Nunc) coated with anti-FLAG antibody (M2 Sigma) diluted at 1:1000, reacted at 22° C. for 1 hour, and then reacted with rabbit-derived anti-Myc antibody (Cell Signaling) diluted at 1:500 at 4° C. for 16 hours.

After washing, peroxidase-labeled anti-rabbit IgG antibody (Jackson Immunolaboratory) was reacted at 22° C. for 30 minutes. Finally, ABS (2,2'-azino-bis-3-ethylbenzothiazoline-6-sulfonate (Roche)) was added to develop color, followed by analysis with a multiplate reader (absorbance: 405 nm, reference: 490 nm).

Half-Life of scFv Protein and Degradation Inhibition Assay

Myc-tagged scFv (scFv-Myc, scFv-Myc-CL1, and scFv-Myc-CMA) was transfected into the cultured cells (HEK293A). 48 hours later, cycloheximide (CHX) was added at a concentration of 100 µg/ml to stop new protein synthesis. Immediately after that, a proteasome inhibitor (lactacystin) and a lysosomal inhibitor (bafilomycin) were added at concentrations of 10 µM and 0.1 µM, respectively, and the cells were collected after 10 and 24 hours, including the control without addition of any compound, and denatured by dissolving them in 2% SDS sample buffer containing 2 mercaptoethanol. Thereafter, detection was performed using an anti-Myc antibody according to the Western blotting method described above, and bands were quantified by a densitometry method.

Analysis of TDP-43 Protein Degradation Efficiency of scFv

TDP-43 labeled with HALO TAG™ (Promega) (TDP-43-Halo) and Myc-labeled scFv (scFv-Myc) were co-expressed by the above method. 48 hours later, the expressed TDP-43-Halo was labeled by addition of 1 µM of diAcFAM ligand (Promega) for 15 minutes, then the culture medium was washed, and the culture was continued in a normal medium. Immediately, 12 hours, and 24 hours after the addition of diAcFAM ligand, the cells were collected with 2% SDS sample buffer, and subjected to 5-20% polyacrylamide gel electrophoresis. Then, the gel was photographed with a fluorescence camera (LAS-3000; FUJIFILM). Thereafter, the gel was transferred to a PVDF membrane for Western blotting, and analyzed.

Time-Lapse Video Microscope Analysis

GFP-labeled TDP-43 (TDP-43-GFP) and scFv-CMA were co-expressed in HEK293A cells using the above method. 24 hours later, Hoechst 33342 (Nacalai Tesque, Inc.) was added to the culture medium to stain the cell nuclei, and continuous shooting was performed every 30 minutes for 48 hours with a time-lapse fluorescence microscope (BZX-710; Keyence, Osaka) using the included software. Four places were randomly selected before the first shooting, and the same places were photographed after that.

Cell Survival and Cell Death Assay

FLAG-tagged TDP-43 and Myc-tagged scFv were co-expressed in the Neuro2a cells in a 96-multiwell plate by the above method. 48 hours later, glycyl-phenylalanyl-amino fluorocoumarin (GF-AFC) and bisalanyl-alanyl-phenylalanyl-rhodamine 110 (bis-AAF-R110) of a commercial live/dead cell quantification kit (MULTITOX-FLUOR™ multiplex cytotoxicity assay; Promega) were simultaneously added and reacted in an incubator for 2 hours. Then, using a fluorescence multiplate reader (Perkin Elmer), live cells were counted at a fluorescence of 400/505 nm, and dead cells were counted at 485/520 nm.

Quantitative PCR Analysis

From the HEK293A cells transfected by the above method, cDNA was prepared using a commercial RNA extraction kit (Invitrogen) and cDNA preparation kit (Invitrogen). According to the protocol of the instruction manual of a SYBER™ Green quantification kit (Toyobo), PCR was performed with a real-time PCR detection system (Bio-Rad), and quantitative analysis was performed using the included software. The primer sequences used are as follows. HSP70: 5'-CAA GAT CAC CAT CAC CAA CG-3' (SEQ ID NO: 25) and 5'-TCG TCC TCC GCT TTG TAC TT-3' (SEQ ID NO: 26); GAPDH: 5'-GCA CCG TCA AGG CTG AGA AC-3' (SEQ ID NO: 27) and 5'-TGG TGG TGA AGA CGC CAG TGG A-3' (SEQ ID NO: 28)

In Utero Electroporation

The uterus was taken out from SJR pregnant mice on the 13.5th day of pregnancy under isoflurane inhalation anesthesia. While holding the uterus, 1 to 2 µL of an expression plasmid of TDP-43-GFP or GFP, scFV-Myc, and mCherry (Takara Bio Inc.) (pCAG-TDP-43-GFP, pCAG-scFv-Myc, pCAG-mCherry) dissolved in clean PBS was visually injected into the fetal lateral ventricle. Then, the outside of the brain was lightly pinched with a round electrode (CUY650P5; Nepagene), the cathode was placed on the plasmid injection side, and electrical stimulation was intermittently applied 5 times (31 V, 50 ms, at 950-millisecond intervals). Thereafter, the uterus was returned to the mother's abdominal cavity, followed by suturing, and the pregnancy was continued.

Method of Immunohistochemical Staining of Mouse Brain Section

After the pregnancy was continued by the above method, the fetus was taken out, and pentobarbital was administered intraperitoneally. Then, 4% PFA was administered transcardially for perfusion fixation. After the brain was taken out, it was further post-fixed in a 4% PFA solution at 4° C. for 16 hours, then embedded in OCT compound (Sakura Finetek Japan Co., Ltd.), and fixed with liquid nitrogen. 12 µm sections were prepared with a cryostat and attached to a MAS-coated slide glass.

In immunostaining, the OCT compound was first removed by washing with 0.1 M PBS-T buffer containing 1% TRITON™-X100, and then PBS-T buffer containing 3% bovine serum albumin (Nacalai Tesque, Inc.) was added for blocking. Thereafter, reaction with a primary antibody was performed at 4° C. for 16 hours, followed by washing. Then, reaction with a fluorescently labeled secondary antibody (FLUOR™ antibody, Invitrogen) was performed at 22° C. for 1 hour, followed by washing. Then, cover glass treatment was performed using a mounting medium (Vector) containing 4'-6 diamidino-2-phenylindole (DAPI). The sections were observed and photographed using a confocal laser microscope (FV1000-D IX81, Olympus Corporation).

Test Example 1: In Vitro Test

Figure 1:
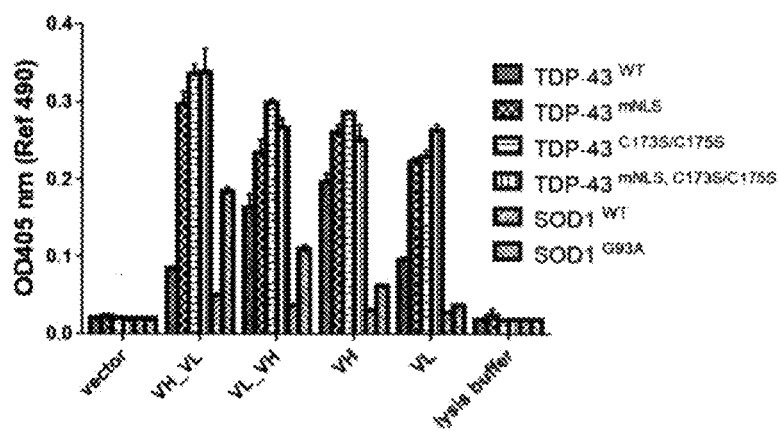
FIG. 1 shows the binding specificity of the antibody fragment to misfolded TDP-43. n=3, data: mean±SD
Figure 2:
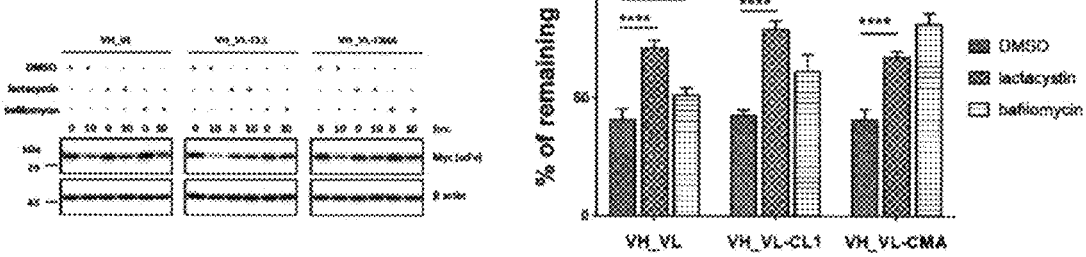
FIG. 2 shows the degradation characteristics of scFv. left: Western blotting, right: a graph showing the percentage of remaining scFv. Each data was standardized with actin. data: mean±SD, from three independent experiments. $*p<0.05$, $****p<0.001$, compared to the DMSO control group. The test is based on Dunnett's two-way analysis of variance. N.S. indicates not significant.

ScFv-Myc and TDP-43 (wild-type, mutated nuclear localization signal type (mNLS), nuclear aggregate-forming mutation type (C173S/C175S), and cytoplasmic aggregate-forming mutation type (mNLS-C173S/C175S)) were expressed in the cultured cells (HEK293A), and the lysate was analyzed by a sandwich ELISA method to quantify the binding of TDP-43 and scFv. The results are shown in FIG. 1.

scFv (untagged, CLI1-taged, and CMA-tagged) was expressed in the cultured cells, and cycloheximide (100 µg/ml) was added to stop protein synthesis. 24 hours later, the cells were collected, and the remaining scFv-Myc was quantified by Western blotting. The results are shown on the right side of FIG. 2.

Figure 3:
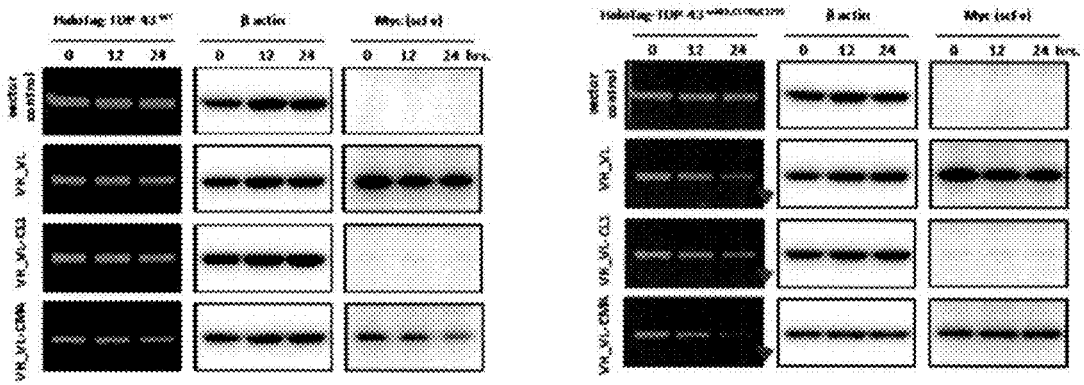
FIG. 3 shows the misfolded TDP-43 degradation characteristics of scFv. For each time data, the densitometry data of fluorescence bands was normalized with that of actin. data: mean±SD, from three independent experiments. $*p<0.005$, $**p<0.001$, compared to the vector control group. The test is based on Dunnett's two-way analysis of variance. N.S. indicates not significant.

HALO-TAG™ TDP-43 (wild-type and cytoplasmic aggregate-forming type (mNLS-C173S/C175S)) was expressed in the cultured cells, and fluorescent Halo ligand was added 24 hours later. 0, 12, and 24 hours later, the cells were collected, applied on SDS-PAGE, analyzed with a fluorescence imaging device, and quantified. The results are shown in FIG. 3.

TDP-43-EGFP (cytoplasmic aggregate type) and scFv were co-expressed in the cultured cells (HEK293A cells), and photographed over time with a time-lapse fluorescence microscope. The number of aggregates per 100 cells, the size of aggregates per cell, and the remaining cells were quantified, and the average value of four fields of view was calculated. The results are shown in the upper part of FIG. 4.

Vector or scFv (untagged, CLI-tagged, and CMA-tagged) was co-expressed with wild-type or misfolded TDP-43 in the cultured cells (Neuro2a), and cell viability and cell cytotoxicity were quantified. The results are shown in the lower part of FIG. 4.

Test Example 2: Induction of Hsp70

TDP-43-FLAG (wild-type and cytoplasmic aggregate-forming type (mNLS-C173S/C175S)) or vector, and scFv-Myc (no signal, CLI, and CMA signal) or vector were co-expressed in the cultured cells (HEK293A), and the cells were collected 48 hours later. cDNA was collected from the cells, and the mRNA of Hsp70 was analyzed by real-time PCR assay. The results are shown on the left side of FIG. 5. Hsp70 was detected in the cell lysate by Western blotting, and protein levels were quantified by densitometry. The results are shown on the right side of FIG. 5.

TDP-43-FLAG was overexpressed with vector, Hsp90, or Hsp70 in the cultured cells (HEK293A), and the cells were solubilized in a surfactant (1% TRITON™ X100), followed by separation into a supernatant and a precipitate. Each was analyzed by Western blotting using an Hsp70 antibody, and the detected bands were quantified by densitometry. The data obtained by dividing the insolubilized TDP-43 by the solubilized TDP-43 are shown in FIG. 6.

Test Example 3: In Vivo Test

TDP-43-GFP and scFv-CMA were transferred into the lateral ventricle of the fetal brain of mice at a gestational age of 13.5 (E13.5), and the pregnancy was continued. On the 16th day of pregnancy, the fetal brain was fixed, and brain sections were prepared and immunostained with an anti-GFP antibody, an anti-ubiquitin antibody, and an anti-phosphorylation TDP-43 antibody. The misfolded TDP-43 is mNLS-TDP-43 C173S/C175S. The results are shown in FIG. 7.

In the same manner as described above, TDP-43-EGFP and scFv-Myc-CMA were transferred into the fetal brain at E13.5, and the pregnancy was continued. The fetal brain was fixed at E16, and brain sections were prepared and immunostained with an anti-GFP antibody and an anti-Myc antibody. The results are shown in FIG. 8.

In the same manner as described above, TDP-43-EGFP, scFv-Myc-CMA, and mCherry were transferred into the fetal brain at E13.5, and the pregnancy was continued. The fetal brain was fixed at E16, and brain sections were prepared and immunostained with an anti-GFP antibody, an anti-Myc antibody, and an anti-mCherry antibody. Then, aggregates were quantified by fluorescence intensity and size. The results of misfolded TDP-43 are shown in FIG. 9, and the results of wild-type TDP-43 are shown in FIG. 10. In the mouse brain expressing wild-type TDP-43, scFv-Myc-CMA did not affect the expression levels of TDP-43.

In the same manner as described above, scFv-Myc-CMA and mCherry were transferred into the fetal brain at E13.5. After pregnancy and delivery, observation was continued until the 21st day. The offspring were normally lactated and weaned, and showed the same growth as the control. On the same day, the brain was fixed, and immunostained with an anti-Myc antibody, an anti-mCherry antibody, an anti-NeuN antibody, an anti-Ibal antibody, and an anti-GFAP antibody. The results are shown in FIG. 11.

The invention claimed is:

1. A modified antibody fragment that binds to misfolded TAR DNA-binding protein of 43 kDa, wherein the modified antibody fragment comprises an antibody fragment and a chaperone-mediated autophagy localizing signal peptide comprising KFREQ (SEQ ID NO: 8) and linked to the C-terminus of the antibody fragment;

the antibody fragment comprising:
- a heavy-chain variable region comprising a heavy-chain CDR 1 consisting of an amino acid sequence GFNIKDYY (SEQ ID NO: 1), a heavy-chain CDR 2 consisting of an amino acid sequence IDPEDGET (SEQ ID NO: 2), and a heavy-chain CDR 3 consisting of an amino acid sequence TIYYYGSRYVDY (SEQ ID NO: 3); and
- a light-chain variable region comprising a light-chain CDR 1 consisting of an amino acid sequence SSISSSY (SEQ ID NO: 4), a light-chain CDR 2 consisting of an amino acid sequence RTS, and a light-chain CDR 3 consisting of an amino acid sequence QQGSSIPLT (SEQ ID NO: 5); and wherein the antibody fragment is a scFv; and
wherein the antibody fragment and the chaperone-mediated autophagy localizing signal peptide are directly bonded, or an amino acid sequence exists between them.

2. The modified antibody fragment according to claim 1, wherein the antibody fragment is a humanized antibody fragment.

3. A nucleic acid encoding the modified antibody fragment according to claim 1.

4. An expression vector comprising the nucleic acid according to claim 3.

5. A method of inducing a heat shock protein in a cell, the method comprising administering the nucleic acid according to claim 3.

6. The method of claim 5, wherein the heat-shock protein is Hsp70.

* * * * *